United States Patent [19]

Rydell et al.

[11] Patent Number: 5,026,371
[45] Date of Patent: Jun. 25, 1991

[54] HANDLE FOR POLYPECTOME SNARE WITH BIPOLAR ELECTRODES

[75] Inventors: Mark A. Rydell, Golden Valley; Brent L. Anderson, Corcoran, both of Minn.

[73] Assignee: Everest Medical Corporation, Minneapolis, Minn.

[21] Appl. No.: 590,783

[22] Filed: Oct. 1, 1990

[51] Int. Cl.$^5$ .............................................. A61B 17/39
[52] U.S. Cl. ........................................ 606/47; 606/48; 606/113
[58] Field of Search ........................ 606/32, 34, 37, 39, 606/40, 41, 45–50, 110–113

[56] References Cited

U.S. PATENT DOCUMENTS

| | | | |
|---|---|---|---|
| 3,955,578 | 5/1976 | Chamness et al. | 606/47 |
| 4,311,143 | 1/1982 | Komiya | 606/47 |
| 4,493,320 | 1/1985 | Treat | 606/47 |
| 4,905,691 | 3/1990 | Rydell | 606/47 |

Primary Examiner—Stephen C. Pellegrino
Assistant Examiner—Steven J. Shumaker
Attorney, Agent, or Firm—Haugen and Nikolai

[57] ABSTRACT

An improved handle for a polypectome snare for use in excising polyps from an internal body cavity. The apparatus generally comprises a radio frequency polypectome snare which includes a hand grip assembly, a flexible tubing assembly capable of fitting within an endoscope, an electrode loop portion and a power supply means. The hand grip assembly is made of molded pieces of inflexible plastic comprising a longitudinal housing portion and a slide member having opposing finger grip members. When the slide member is in its most proximal position, the electrode loop portion is withdrawn into the flexible tubing. As the slide member is advanced toward the distal end of the longitudinal housing, the electrode wires are advanced out of the flexible tubing, forming a loop that can be placed around the stem of a polyp. Once again withdrawing the loop into the end of the flexible tubing while simultaneously applying RF voltage shears the polyp at its base. The slide member and housing are designed to be molded using conventional equipment, a significant improvement over the prior art in which several pieces had been proportioned by hand. This is possible because the molded housing of the hand grip is fitted with a longitudinal slot which receives the molded slide member in such manner that the only movement permitted is proximal or distal to the tubing. The electrode wires are affixed to a molded slide block on the slide member and are encased in rigid conductor tubes that extend the full length of the housing. A molded guide and retaining hub further stabilize the wires in the distal end of the housing. The electrode wires thus remain insulated from one another and do not short or arc because this stabilized arrangement at the distal end of the housing works in tandem with the stabilizing aspect of the slide member slide block to prohibit twisting of the wires or conductor tubes.

7 Claims, 1 Drawing Sheet

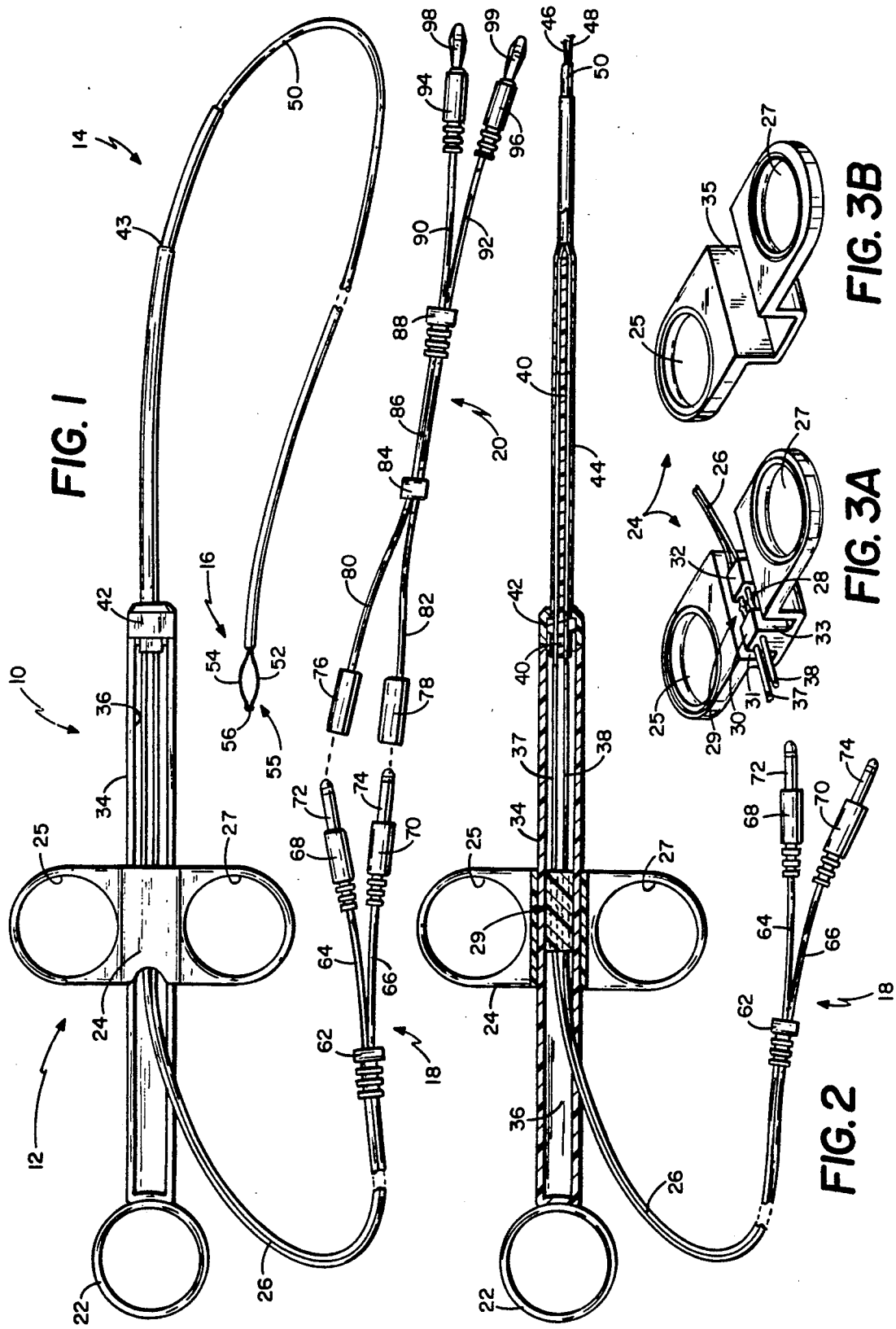

HANDLE FOR POLYPECTOME SNARE WITH BIPOLAR ELECTRODES

BACKGROUND OF THE INVENTION

I. Field of the Invention

This invention relates generally to electrosurgical apparatus, and more particularly to an improved handle device for a polypectome snare for use in excising polyps from an internal body cavity.

II. Discussion of the Prior Art

Polypectome snares are electrically powered devices designed for the removal of small growths from the lining of internal body cavities. The growth, or polyp, is encircled by the snare, then sheared off by electrocautery action.

The U.S. Pat. No. 4,905,691 of Rydell describes a bipolar polypectome snare in which the electrodes are insulated from one another by means of two concentric tubes. One tube encloses one electrode wire and this tube is positioned within the second tube which also encloses the other wire. An RF voltage is applied by a power supply such that when the loop of the snare is placed around a polyp and tightened, the polyp is excised. Another design of a bipolar polypectome snare is disclosed in co-pending application Ser. No. 07/554,835 of Rydell, wherein both electrode wires are housed in tubing. This tubing may either be a solid rod in which parallel bores receive the electrode wires or it may be two, separate small diameter tubes, each of which contains an electrode wire and which are disposed inside a third tube which serves as a retainer.

In U.S. Pat. No. 4,311,143 to Komiya, there is described the construction of a bipolar electrosurgical polypectome snare which comprises an elongated, flexible plastic tube whose outside diameter is sufficiently small to permit it to pass through the lumen of an endoscope and affixed to the distal end of the tube is a first electrode in the form of an annular metallic cap. The second electrode comprises a wire loop which can be extended and retracted relative to the distal end of the tubular body. When inserted through the lumen of an endoscope, it can be made to loop around the polyp to be excised and then by manipulating a hand grip member, the loop can be drawn tight about the neck of the polyp as RF energy is applied between the annular cap and the wire loop. The tissue comprising the polyp completes the circuit between the two electrodes and with sufficient power applied, the stem of the polyp will eventually be cut through. The hand grip member of the instrument is not described in detail.

The Treat U.S. Pat. No. 4,493,320 describes a polypectome snare having a bi-lumen tube dimensioned to fit through an endoscope. It has a pair of wires routed through each of the lumens which extend beyond the distal end thereof, where they are joined with an insulating tip member to form a loop. Thus, portions of the wires themselves become the active bipolar pair. The hand grip used to open and close the loop consists of prongs which extend from the face of a slide block that is positioned in the base of the device. In this manner, the block can be manually operated to slide along the longitudinal axis of the base. As the handle moves the slide block, the snare wires are caused to slide in the tube so as to expand or retract the surgical loop that extends from the distal end of the tube.

The afore-referenced Rydell Patent '691 and pending application '835 teach a polypectome snare with bipolar electrodes in which a pair of wire electrodes is routed through the lumens of first and second tubes. These tubes are dimensioned to fit inside the lumen of an endoscope. When the first tube is placed inside the second tube, rotation of the proximal end of one of the two wires is permitted but an attempt to rotate the loop does not cause twisting of the wires as it did in the prior art. Furthermore, the handle was redesigned to include finger holes affixed to a slide block and to the base of the device. The thumb is inserted into the hole provided at the proximal end of the base. The index and middle fingers are then inserted into the two holes provided in the slide block. As the slide block is opposably advanced, the loop of the snare is caused to open, since the electrode wires are mounted on the slide block. Conversely, the loop will close around the base of the polyp and cauterize it as the two sets of finger holes are drawn together.

Problems exist with the Treat and Rydell devices. In the Treat U.S. Pat. No. 4,493,320, an elongated base member is fitted with a slide block which includes a handle. The handle consists of two prongs and a loop. It is possible that the surgeon's hand could slip on the prongs as his attention is drawn away from his hand, as when he views the endoscope screen.

The Rydell improvement in U.S. Pat. No. 4,905,691 addressed this tendency for slipping by providing secure finger holes. The surgeon is then free to focus his attention on polyp removal as he is guided by viewing the endoscope screen. The co-pending improvement provides the same functional handle which did not short, but both are expensive and labor-intensive to produce, thus precluding disposability.

The present invention is applicable to all of these devices, since it provides an improved handle that will interface with each of applicant's earlier designs. This is significant because it has been found that utilization of bipolar electrodes instead of a monopolar arrangement has, in the past, created difficulty in proper handle design. Specifically, the handle must be designed in a manner that prevents any rotation of the wire which might permit arcing or cause a dead short proximal of the working loop or snare. This must be accomplished economically yet in a way that permits easy assembly.

SUMMARY OF THE INVENTION

The present invention provides an arrangement for inexpensive stabilization of the electrode wires within the handle of a polypectome device. A significant advantage attendant to the construction of the preferred embodiment when compared to the device of the applicant's earlier patent '691 is that the wires remain physically spaced from one another in a manner that enhances stability as the handle of the snare device is manipulated. Such stability prohibits shorts or rotation, allowing proper function of the device. This improved handle design is significantly easier to produce with less expensive materials, thus permitting the present device to be totally disposable, avoiding the need for meticulous cleaning and sterilization following use.

DESCRIPTION OF THE DRAWINGS

Further features and advantages of the invention will become apparent to those skilled in the art from the following detailed description of a preferred embodiment, especially when considered in conjunction with the accompanying drawings in which like numerals in the several views refer to corresponding parts.

FIG. 1 is a plan view of the polypectome snare constructed in accordance with the present invention;

FIG. 2 is a side cut-away view of the proximal end portion of the polypectome snare of FIG. 1;

FIGS. 3A and 3B show a cut-away view of the two halves of the slide block.

DESCRIPTION OF THE PREFERRED EMBODIMENT

Referring to FIG. 1, there is indicated generally by numeral 10 the radio frequency (RF) polypectome snare constructed in accordance with the present invention. It is seen to include a hand grip assembly, generally designated as 12 and preferably formed by molding its pieces from an inflexible plastic material. A thin, flexible tubing assembly, designated generally as 14, extends from the hand grip 12 and is preferably formed from a flexible plastic such as teflon. A snare assembly, generally designated as 16, is comprised of a pair of uninsulated wires joined at their distal ends by an insulator, such as a ceramic bead. Insulated wires lead from the hand grip to an RF source and are generally designated as 18. An extension cord/adapter 20 is also provided to accommodate the various receptacles available on the market.

Beginning with the portions 14 and 16 of the polypectome snare that are adapted to pass within the lumen of an endoscope, the portion 14 is seen to include a first, outer tubular member 50, preferably formed from a flexible plastic material such as teflon, polyethylene or other medical grade plastic. As described in greater detail in applicant's U.S. Pat. No. 4,905,691, and co-pending application Ser. No. 07/554,835, a lumen extends the full length of the outer tubular member 50 and disposed within this lumen are a second elongated flexible plastic tubular member 46 and a third elongated flexible plastic tubular member 48 (FIG. 2). These are generally coextensive in length with the outer tube 50.

The electrode wires 52 and 54 have their proximal ends crimped within tubular reinforcing rods 37 and 38, as described in greater detail hereinafter. With no limitation intended, these rods 37 and 38 are preferably made of stainless steel. At least the distal end portions of the wires 52 and 54 are bare metal and are mechanically coupled, but electrically insulated from one another at their distal ends by means of a ceramic bead 56. The conductors are preferably stainless steel braid and are preformed to exhibit a memory property at their distal end so that when unconstrained they will cooperate to form an open loop. The electrical current from the RF generator can be impressed on the wires 52 and 54 while still permitting the loop to be closed by retracting the hand grip assembly 12.

In FIG. 2, the slide 24 of the hand grip 12 is illustrated as being in a central position relative to the slot 36. When slide 24 is moved to its most rearward or proximal position, the loop 55 defined by the distal end portions of the conductors 52 and 54 will be retracted to the point where the ceramic tip 56 abuts the distal end of the inner tube 46. By allowing the ceramic tip 56 to retract slightly into tube 50 it is brought into contact with tubes 46 and 48, thereby assuring complete cutting of the polyp. It will be appreciated, however, that when the slide 24 is pushed forward, i.e., in the distal direction, the wires 52 and 54 are made to extend outward beyond the distal end of the tubes 46 and 48, exposing the loop 55.

With continued reference to FIG. 2, the proximal end of the outer tubular member 50 is surrounded by a length of heat shrink tubing 4 for added reinforcement and support. The hand grip assembly 12 is affixed to the proximal end of the tubes 44, 46, 48 and 50. It consists of a molded plastic housing member 34 of generally rectangular cross-section having a longitudinal slot 36 formed on the underside thereof. Fitted onto the housing 34 is a slide member 24 having a slide block 29. As shown in FIG. 3A, block 29 has distal 30 and proximal 32 retention portions, adapted to ride in the longitudinal slot 36 formed in the housing 34. Integrally molded with the slide member 24 and extending laterally on opposed sides of the housing 34 are finger grip members 25 and 27, here shown as being annular in shape for receiving the forefinger and index finger of one hand. An additional ring 22 is affixed to the proximal end of the housing 34 and is intended to receive the user's thumb therein.

The slide block 29 includes a channel or, alternatively, a pair of parallel bores, in which is fitted a pair of crimp tubes 28, preferably made of copper. The conductive tubular rods 37 and 38 fit into the crimp tubes as do the electrode wires 52 and 54 and the lead wires 26, used to join the polypectome snare to the RF generator (not shown).

The conductor tubes 37 and 38 may be approximately 12 cm in length and extend from the crimped tubing connector 28 along the length of the housing 34 such that they protrude approximately 1 cm beyond the distal end of this housing when the slide member assembly 24 is retracted to the most proximal position along the housing 34.

A form-fit plastic retainer 40 receives the two conductive tubes 37 and 38. This retainer 40 consists of a keyway-type hub at its proximal end. This hub (not shown) is a cube approximately 8 mm long and has one bore for each of the electrical conductor tubes 37 and 38. A length of the retainer 40 extends approximately 9.5 cm beyond this hub and has two semicircular or arcuate grooves on opposing sides to receive both the conductor tubes 37 and 38 containing the wires 52 and 54 therein. The portion of the retainer containing the grooves is molded as a circular rod having a diameter slightly greater than that of the outer tubing 50, which abuts the grooved rod at its distal end. The retainer 40 and outer tube 50 are held together at 43 by being encased in high-grade heat shrink tubing 44 that runs from the distal side of the cube hub of the retainer 40 to approximately 6 cm beyond the distal end of the retainer. In this manner, the retainer 40 and outer tube 50 cannot be pulled apart.

A square plastic hub 42 is fed toward the proximal end of the heat shrink tubing 44 after assembly is complete. When glued onto a small extension of the distal end of the housing 34, it traps the cubic portion of the retainer 40 in a manner that prohibits even slight rotation. The only movement permitted is proximal and distal sliding of the slide member assembly 24 along the track created in the housing 34.

The slide member assembly 24 is preferably composed of two sections of rigid molded plastic, as shown in FIGS. 3A and 3B. As previously explained, wiring 26 from an RF source (not shown) is mated with electrode wires 52 and 54 by crimping the crimp tubing 28 upon itself. Referring to FIG. 3A, the wiring 26 is stabilized by slide block 29 which is of rigid plastic into which a channel or, alternatively, two holes have been bored to receive the crimp tubes and each of the two wires from the RF source. The electrode wires 52 and 54 contained in the rigid conductor tubes 37 and 38 fit into the crimp tubes held in slide block 29. Retention portions 30 and 32 of slide block 29 are molded in such a manner that troughs 31 and 33 are formed between them and the inner side walls of the slide member 24. These troughs 31, 33 are dimensioned to permit clearance of the walls of housing 34, so that when placed together, the retainer portions 30 and 32 fit inside the longitudinal slot 36 while the finger hole portions 25 and 27 fit just outside the wall of the housing 34. This permits the slide member assembly 24 to be shifted to any position on the length of the housing 34.

Mating with the molded section shown in FIG. 3A is the molded section shown in FIG. 3B. This section features a larger trough 35, dimensioned to encase the outer walls of the housing 34. When these two sections 3A and 3B are fused together, the result is a solid slide member assembly that will move the length of the longitudinal slot 36.

Insulated wires leading from the hand grip assembly are generally designated as 18 in FIGS. 1 and 2. In the preferred embodiment, wire 26 has a reinforcing hub 62 approximately 30 cm from the proximal end of the assembly 24. Proximal to this point, the wire 64 and 66 are split from each other. Each has a reinforcing hub 68 and 70 forming a part of standard male connectors 72 and 74. It is preferred to use standard male ECG cable connectors, but those familiar with the art may envision many acceptable alternatives.

FIG. 1 also shows an extension cord assembly 20 which is included to permit ease of interfacing the instrument 10 with the many electrocautery power generators available on the market. Standard female jacks 76 and 78 mate with pins 72 and 74. Each jack 76 and 78 is on a separate wire 80 and 82 which are joined at hub 84. Wire 86 may be of any length desired, as determined by the location of reinforcing hub 88, where segment 86 splits into the individual wires 90 and 92. These wires 90 and 92 terminate in hubs 94 and 96, fitted with male connector pins 98 and 99 of a compatible type.

In summary, a radio frequency generator will have its output connected by cables 26 and 86 to the terminals encased in the crimped tubing 28. In that the wires 52 and 54 are fully contained over most of their length within separate plastic insulating tubes, they remain shielded against short circuiting. With the slide in its most proximal position, the distal end portions of conductors 52 and 54 will each be retracted into the lumen of its respective tube. In this configuration, the snare assembly 10 can readily be inserted through an endoscope into the body organ from which the polyps are to be removed. By pushing the slide member 24 in the distal direction, the wires 52 and 54 comprising the bipolar electrodes will exit the distal end of the tubes 46, 48 and 50 and, because of the memory property of the wires employed, will spring into an open loop 55, as best illustrated in FIG. 1. By manipulating the loop 55, it can be made to rotate into alignment with the polyp and made to surround the stem thereof. When the RF power source is energized and the slide member 24 is retracted in the proximal direction to again close the loop, the electrodes 52 and 54 will encircle the stem of the polyp to the point where an arc discharge is created, thereby rapidly severing the stem tissue.

An important feature of the preferred embodiment is that the hand grip 12 of the snare 10 permits manufacture by standard molding methods. The prior designs required much hand matching and thus were too expensive to be considered disposable. This improvement has been accomplished while maintaining the advantages of applicant's prior designs, such as prevention of crossing and shorting of the electrodes.

The polypectome snare of the present invention can be fabricated from a variety of available materials. For example, various medical grade plastics may be employed in molding the hand grip portion 12 with polycarbonate being preferred. The tubes 46, 48 and 50 may be extruded polyethylene, polyurethane, polypropylene or Teflonφ, with Teflon being preferred. The electrode conductors 52 and 54 are preferably formed from braided strands of stainless steel, although other materials may be used as well and because of the manner in which they are isolated from one another in traversing the length of the tubes, need not themselves be coated with an insulator.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modification, both as to the equipment details and operating procedures, can be accomplished without departing from the scope of the invention itself.

What is claimed is:

1. In an electrosurgical instrument of the type including a first elongated flexible plastic tube having a proximal end, a distal end and at least one lumen extending from said proximal end to said distal end and first and second wires extending through said lumen and longitudinally displaceable therein, said wires being insulatedly spaced from one another throughout the majority of their length and including an uninsulated segment comprising electrodes which when unconstrained forms an open loop, an improved manually operable handle means for imparting longitudinal displacement to said first and second wires within said lumen of said tube comprising:

(a) a rigid housing of a predetermined length having a proximal end, a distal end and a longitudinal slot formed between said proximal and distal ends and including a thumb receiving member affixed to said proximal end, said housing being attached to said proximal end of said first tube;

(b) a slide member including a slide block fitted into said longitudinal slot and a pair of extending finger receiving members extending oppositely and transversely from said slide block, the walls of said slot constraining said slide block to longitudinal movement between said proximal and distal ends of said slot with at least one longitudinally extending channel formed in said slide block;

(c) first and second electrical lead means for applying power to said first and second wires;

(d) means disposed in said channel(s) for attaching said lead means to said first and second wires whereby longitudinal displacement of said slide member in said slot in the distal direction causes said electrode segments to extend beyond said distal end of said tube opening said loop and longitudinal displacement of said slide member causes said electrode segments to retract into said distal end of said tube, closing said loop; and
(e) second and third tubes individually containing said first and second wires wherein said second and third tubes are contained within the lumen of said first tube.

2. The electrosurgical instrument as in claim 1 wherein the proximal ends of said first, second and third tubes are joined to said housing.

3. The electrosurgical instrument as in claim 1 wherein said housing includes an insulating guide extending outwardly from the distal end of said rigid housing, said guide including arcuate grooves running the length thereof for supporting said first and second wires therein and a retainer hub means fitted to encompass the distal end of said rigid housing for securing said guide to said housing.

4. The electrosurgical instrument as in claim 1 wherein said first elongated flexible plastic tube is encased in a length of shrink tubing at its proximal end for providing strain relief.

5. The electrosurgical instrument as in claim 1 wherein:
(i) the proximal end of said first wire is encased in a first tubular rod and having the proximal end of this wire and rod combination crimped to the distal end of said first electrical lead means;
(ii) the proximal end of said second wire is encased in a second tubular rod and having the proximal end of this wire and rod combination crimped to the distal end of said second electrical lead means; and
(iii) said first and second tubular the length of said housing.

6. The electrosurgical instrument as in claim 3, wherein:
(i) the proximal end of said first were is encased in a first tubular rod and having the proximal end of this wire and rod combination crimped to the distal end of said first electrical lead means;
(ii) the proximal end of said second wire is encased in a second tubular rod and having the proximal end of this wire and rod combination crimped to the distal end of said second electrical lead means; and
(iii) said first and second tubular rods extend beyond the length of said housing.

7. The electrosurgical instrument as in claim 6 wherein said first and second tubular rods are fitted into said insulating guide extending outwardly from the distal end of said housing.

* * * * *

UNITED STATES PATENT AND TRADEMARK OFFICE
CERTIFICATE OF CORRECTION

PATENT NO. : 5,026,371

DATED : June 25, 1991

INVENTOR(S) : Mark A. Rydell, et al.

It is certified that error appears in the above-identified patent and that said Letters Patent is hereby corrected as shown below:

Column 8, Line 7, after the word "tubular" please insert -- rods extend beyond --.

Column 8, Line 12, delete the word "were" and insert -- wire --.

Signed and Sealed this

Sixth Day of October, 1992

*Attest:*

DOUGLAS B. COMER

*Attesting Officer*　　　　*Acting Commissioner of Patents and Trademarks*